US012582643B2

(12) United States Patent
Nefedova et al.

(10) Patent No.: US 12,582,643 B2
(45) Date of Patent: Mar. 24, 2026

(54) TASQUINIMOD OR A PHARMACEUTICALLY ACCEPTABLE SALT THEREOF FOR USE IN COMBINATION THERAPY

(71) Applicants: ACTIVE BIOTECH AB, Lund (SE); THE WISTAR INSTITUTE OF ANATOMY AND BIOLOGY, Philadelphia, PA (US)

(72) Inventors: Yuliya Nefedova, Villanova, PA (US); Marie Törngren, Genarp (SE); Helena Eriksson, Torna-Hällestad (SE); Dmitry Gabrilovich, Villanova, PA (US); Fabien Schmidlin, Mondeville (FR)

(73) Assignees: ACTIVE BIOTECH AB, Lund (SE); THE WISTAR INSTITUTE OF ANATOMY AND BIOLOGY, Philadelphia, PA (US)

( * ) Notice: Subject to any disclaimer, the term of this patent is extended or adjusted under 35 U.S.C. 154(b) by 822 days.

(21) Appl. No.: 17/802,124

(22) PCT Filed: Mar. 3, 2021

(86) PCT No.: PCT/EP2021/055337
§ 371 (c)(1),
(2) Date: Aug. 24, 2022

(87) PCT Pub. No.: WO2021/175924
PCT Pub. Date: Sep. 10, 2021

(65) Prior Publication Data

US 2023/0085883 A1 Mar. 23, 2023

Related U.S. Application Data

(60) Provisional application No. 63/148,522, filed on Feb. 11, 2021, provisional application No. 62/984,474, filed on Mar. 3, 2020.

(30) Foreign Application Priority Data

Mar. 3, 2020 (EP) .................................... 20160815

(51) Int. Cl.

| | |
|---|---|
| ***A61K 31/4704*** | (2006.01) |
| ***A61K 31/407*** | (2006.01) |
| ***A61K 31/454*** | (2006.01) |
| ***A61K 31/573*** | (2006.01) |
| ***A61K 31/69*** | (2006.01) |
| ***A61K 38/06*** | (2006.01) |
| ***A61K 38/07*** | (2006.01) |
| ***A61K 39/395*** | (2006.01) |
| ***A61P 35/00*** | (2006.01) |
| *A61K 39/00* | (2006.01) |

(52) U.S. Cl.
CPC ........ *A61K 31/4704* (2013.01); *A61K 31/407* (2013.01); *A61K 31/454* (2013.01); *A61K 31/573* (2013.01); *A61K 31/69* (2013.01); *A61K 38/06* (2013.01); *A61K 38/07* (2013.01); *A61K 39/3955* (2013.01); *A61P 35/00* (2018.01); *A61K 2039/505* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,225,539 | A | 7/1993 | Winter |
| 5,229,275 | A | 7/1993 | Goroff |
| 5,545,806 | A | 8/1996 | Lonberg et al. |
| 5,545,807 | A | 8/1996 | Surani et al. |
| 5,565,332 | A | 10/1996 | Hoogenboom et al. |
| 5,567,610 | A | 10/1996 | Borrebaeck et al. |
| 5,573,905 | A | 11/1996 | Lerner et al. |
| 5,585,089 | A | 12/1996 | Queen et al. |
| 5,591,669 | A | 1/1997 | Krimpenfort et al. |
| 5,598,369 | A | 1/1997 | Chen et al. |

(Continued)

FOREIGN PATENT DOCUMENTS

| | | | |
|---|---|---|---|
| EP | 2050764 | A1 | 4/2009 |
| WO | WO 90/07861 | A1 | 7/1990 |

(Continued)

OTHER PUBLICATIONS

De Veirman 2016 (Blood, 2016, 128(22): 3248).*
De Veirman 2017 (Cancer Immunology Research, 2017, 5(10):839-846).*
Kapoor et al (Seminars in Hematology, 2012, 49:228-242).*
Larocca et al (Oncotarget, 2017, 8:60656-60672).*
Palumbo et al (NEJM, 2016, 375:754-766).*
Dimopoulos et al (NEJM, 2016, 375:1319-1331).*

(Continued)

*Primary Examiner* — Laura B Goddard
(74) *Attorney, Agent, or Firm* — James S. Keddie; Bozicevic, Field & Francis LLP

(57) ABSTRACT

A combination comprising tasquinimod, or a pharmaceutically acceptable salt thereof, and at least one further compound selected from a proteasome inhibitor, an immunomodulatory imide, and an antibody, for use as a in the treatment of multiple myeloma. A kit comprising tasquinimod and a package insert with instructions for using tasquinimod in combination with at least one further compound selected from a proteasome inhibitor, an immunomodulatory imide, and an antibody, to treat multiple myeloma in an individual. Tasquinimod for use in the treatment of multiple myeloma, in combination with a further compound selected from a proteasome inhibitor, an immunomodulatory imide, and an antibody.

13 Claims, 4 Drawing Sheets

(56) References Cited

U.S. PATENT DOCUMENTS

| | | | |
|---|---|---|---|
| 5,693,761 A | 12/1997 | Queen et al. | |
| 5,693,762 A | 12/1997 | Queen et al. | |
| 5,859,205 A | 1/1999 | Adair et al. | |
| 6,150,584 A | 11/2000 | Kucherlapati et al. | |
| 9,956,212 B2 * | 5/2018 | Liberg ................. | A61K 31/167 |

FOREIGN PATENT DOCUMENTS

| | | |
|---|---|---|
| WO | WO 99/55678 A1 | 11/1999 |
| WO | WO 00/03991 A1 | 1/2000 |
| WO | WO 01/30758 A1 | 5/2001 |
| WO | WO 03/106424 A1 | 12/2003 |
| WO | WO 2008/057456 A2 | 5/2008 |
| WO | WO 2012/004338 A1 | 1/2012 |
| WO | WO 2012/175541 A1 | 12/2012 |
| WO | WO 2016/042112 A1 | 3/2016 |
| WO | WO 2016/067010 A1 | 5/2016 |
| WO | WO 2016/078921 A1 | 5/2016 |
| WO | WO 2016/146329 A1 | 9/2016 |
| WO | WO 2018/075807 A1 | 4/2018 |
| WO | WO 2019/089832 A1 | 5/2019 |

OTHER PUBLICATIONS

De Veirman et al., "Extracellular S100A9 Protein in Bone Marrow Supports Multiple Myeloma Survival by Stimulating Angiogenesis and Cytokine Secretion", Cancer Immunology Research, 2017, 5(10): 839-846.

Engelhardt et al., "Treatment of relapsed and refractory multiple myeloma", Onkologe, 2018, 24(8): 613-624.

Greenstein et al., "Characterization of the MM.1 human multiple myeloma (MM) cell lines: A model system to elucidate the characteristics, behavior, and signaling of steroid-sensitive and -resistant MM cells", Experimental Hematology, 2003, 31: 271-282.

Harmsen et al., "Properties, production, and applications of camelid single-domain antibody fragments", Appl Microbiol Biotechnol, 2007, 77: 13-22.

Kohler et al., "Continuous cultures of fused cells secreting antibody of predefined specificity", Nature, 1975, 256: 495-497.

Lin et al., "EP896 Inhibition of S100A9 with Tasquinimod Demonstrates Potent Anti-Tumor Activity in Pre-Clinical Models of Multiple Myeloma", HemaSphere, 25th Congress of the European Hematology Association Virtual Edition, 2020, 4:S1, p. 403.

Nakhle et al., "Tasquinimod modulates tumor-infiltrating myeloid cells and improves the antitumor immune response to PD-L1 blockade in bladder cancer", OncoImmunology, 2016, 5(6), e1145333, 15 pages.

Quach et al., "Lenalidomide in multiple myeloma: Current status and future potential", American Journal of Hematology, 2012, 87(12): 1089-1098.

Ramachandran et al., "A Novel Agent Tasquinimod Demonstrates a Potent Anti-Tumor Activity in Pre-Clinical Models of Multiple Myeloma", Blood, 2014, 124(21).

Vogl et al., "A Phase 1 Study of Tasquinimod in Patients with Relapsed or Refractory Multiple Myeloma", Blood, Nov. 2020, 136 (Supplement 1): 17-18.

Wu et al., "Humanization of a Murine Monoclonal Antibody by Simultaneous Optimization of Framework and CDR Residues", J. Mol. Biol., 1999, 294: 151-162.

De Veirman et al., "Myeloid-derived suppressor cells as therapeutic target in hematological malignancies", Frontiers in Oncology, Frontiers Research Foundation, 2014, 4(349): 1-11.

Nie et al., "Advance in the drug therapy of multiple myeloma", Chinese Clinical Oncology, Apr. 2018, 23(4): 367-372.

* cited by examiner

TASQUINIMOD OR A PHARMACEUTICALLY ACCEPTABLE SALT THEREOF FOR USE IN COMBINATION THERAPY

CROSS-REFERENCE TO RELATED APPLICATIONS

This application is a § 371 national phase of International Application No. PCT/EP2021/055337, filed on Mar. 3, 2021, which claims the benefit of European Application No. 20160815.5, filed on Mar. 3, 2020, U.S. Application No. 62/984,474, filed on Mar. 3, 2020, and U.S. Application No. 63/148,522, filed on Feb. 11, 2021, all of which applications are incorporated by reference herein.

FIELD OF THE INVENTION

The present invention relates to combinations of the compound 4-hydroxy-5-methoxy-N,1-dimethyl-2-oxo-N-[4-(trifluoromethyl)phenyl]-1,2-dihydroquinoline-3-carboxamide (tasquinimod), or a pharmaceutically acceptable salt thereof, and one or more further compounds. More particularly, the invention relates to such combinations, where such one or more further compounds are selected from a proteasome inhibitor, an immunomodulatory imide, and an antibody. The invention further relates to tasquinimod for use in combination with one or more further compounds, in the treatment of cancer, e.g. multiple myeloma.

BACKGROUND OF THE INVENTION

Tasquinimod and a method for its preparation were described in International Applications No. PCT/SE99/00676, published as WO 99/55678 and No. PCT/SE99/01270, published as WO 00/03991, which applications also disclosed the utility of tasquinimod and some other quinoline carboxamides for the treatment of diseases resulting from autoimmunity, such as multiple sclerosis, insulin-dependent diabetes mellitus, systemic lupus erythematosus, rheumatoid arthritis, inflammatory bowel disease and psoriasis and, furthermore, diseases where pathologic inflammation plays a major role, such as asthma, atherosclerosis, stroke and Alzheimer's disease.

Processes for preparing tasquinimod also have been described in International Application No. PCT/SE2003/000780, published as WO 03/106424 and in International Application No. PCT/EP2011/061490, published as WO 2012/004338. A deuterated form of tasquinimod was described in International Application No. PCT/EP2012/061798, published as WO 2012/175541.

The use of various quinoline carboxamides for the treatment of cancer, more particularly solid cancers, such as prostate cancer and breast cancer, was disclosed in International Application No. PCT/SE00/02055, published as WO 01/30758. It has been found that these compounds bind to and inhibit the interactions of an immunomodulatory protein (S100A9), which protein promotes tumor development, influences suppressive and pro-angiogenic cells in the tumor microenvironment and participates in the establishment of pre-metastatic niches.

International Application No. PCT/EP2015/075769, published as WO 2016/078921, discloses tasquinimod for use in the treatment of leukemia including acute lymphoblastic leukemia, acute myeloid leukemia, chronic lymphocytic leukemia and chronic myeloid leukemia. International Application No. PCT/EP2015/071391, published as WO 2016/042112, discloses tasquinimod for use in the treatment of multiple myeloma. International Application No. PCT/EP2016/053288, published as WO 2016/146329, discloses tasquinimod for use in combination with a PD-1 and/or PD-L1 inhibitor in the treatment of cancer, in particular bladder cancer.

The general term "cancer" covers a large number of malignant diseases, which may be classified in two ways: by the type of tissue in which the cancer originates (histological type) and by primary site, or the location in the body where the cancer first developed. The international standard for the classification and nomenclature of histologies is the International Classification of Diseases for Oncology. From a histological standpoint cancers may be grouped into six major categories, viz. carcinoma, sarcoma, myeloma, leukemia, lymphoma and so-called mixed types.

Multiple myeloma (MM) is a cancer of plasma cells in the bone marrow. Normally, plasma cells produce antibodies and play a key role in immune function. In MM, collections of abnormal plasma cells accumulate in the bone marrow and interfere with the production of normal blood cells. Symptoms of MM are skeletal (bone) pain and fractures, anemia, infections, and other complications, such as polyneuropathy and renal insufficiency. MM is the second most common hematological malignancy, and still its exact causes remain unknown.

Multiple myeloma remains an incurable and debilitating disease and patients with multiple myeloma eventually relapse. The remission duration in relapsed multiple myeloma decreases with each regimen. Treatment of multiple myeloma therefore presents a special therapeutic challenge. While new treatments in recent years have greatly improved prognosis and survival of multiple myeloma patients, disease progression is still common after achievement of complete remission.

Multiple myeloma can be treated using drugs, which can be given by mouth or directly into the bloodstream. These systemic therapies can reach cancer cells anywhere in the body. Example of systemic drugs to treat multiple myeloma are corticosteroids, such as dexamethasone and prednisone, which form an important part of the treatment of multiple myeloma. Multiple myeloma can also be treated by use of immunomodulatory drugs such as thalidomide, lenalidomide and pomalidomide. Multiple myeloma is also treated with different proteasome inhibitors and antibodies targeting CD38 and BMCA.

MM can also be treated using chemotherapy, which may optionally be followed by autologous stem cell transplantation (SCT). In SCT, stem cells are removed from the patient, and are frozen and stored. Usually, the patient first has undergone a high-dose chemotherapy, which destroys both healthy cells in the bone marrow and the plasma cells causing the disease, after which the removed stem cells are returned to the patient, to produce new, healthy blood cells in the bone marrow. A patient having undergone a SCT usually must take maintenance therapy for up to 2 years, e.g. with thalidomide or lenalidomide. SCT does not cure MM, it can only lead to longer survival. Furthermore, SCT can cause serious complications, especially vulnerability to infections.

MM also may be treated by chemotherapy only, in particular in patients at higher risk for complications from SCT. In that case, the chemotherapy drug often is used in combination with other drugs to reduce chemotherapy side effects, such as corticosteroids. Finally, MM also may be treated by radiation therapy.

If myeloma does not respond to initial therapy or if relapse occurs soon after the completion of initial therapy, the myeloma is considered to be refractory, or resistant to the treatment. In such case, resuming the same treatment by itself will generally not be effective, and an additional drug may be added to the treatment regimen, or a different combination of drugs may be used as second-line therapy. This second-line treatment may have to be followed by a third-line treatment in case of further relapse, and so on.

Presently, MM is not considered curable. In 2010, less than 45% of US patients with diagnosed MM survived for more than 5 years after diagnosis, according to data from the National Cancer Institute at the National Institute of Health. It is obvious that there still remains an urgent need for new treatment options for MM.

A proteasome inhibitor (PI) is a compound that blocks the action of proteasomes, the cellular complexes that break down proteins, in particular proteins that are involved in cell division. There are several known classes of PIs, e.g. peptide boronic acids or pharmaceueticaliy acceptable salts thereof (boronates), peptide aldehydes, peptide vinyl sulfones, peptide epoxyketones, and β lactone inhibitors. The first known PI used in therapy was bortezomib ([(1R)-3-methyl-1-[[(2S)-3-phenyl-2-(pyrazine-2-carbonylamino)propanoyl]amino]butyl]-boronic acid). Bortezomib acts as a reversible boronic acid inhibitor of the chymotrypsin-like activity of the proteasome. Later generation PIs include carfilzomib ((2S)-4-methyl-N-[(2S)-1-[[(2S)-4-methyl-1-[(2R)-2-methyloxiran-2-yl]-1-oxopentan-2-yl]amino]-1-oxo-3-phenylpropan-2-yl]-2-[[(2S)-2-[(2-morpholin-4-ylacetyl)amino]-4-phenylbutanoyl]amino]pentanamide) and oprozomib (N-[(2S)-3-methoxy-1-[[(2S)-3-methoxy-1-[[(2S)-1-[(2R)-2-methyloxiran-2-yl]-1-oxo-3-phenylpropan-2-yl]amino]-1-oxopropan-2-yl]amino]-1-oxopropan-2-yl]-2-methyl-1,3-thiazole-5-carboxamide), both irreversible epoxyketone proteasome inhibitors, as well as ixazomib ([(1R)-1-[[2-[(2,5-dichlorobenzoyl)amino]acetyl]amino]-3-methylbutyl]boronic acid) and delanzomib ([(1R)-1-[[(2S,3R)-3-hydroxy-2-[(6-phenylpyridine-2-carbonyl)amino]-butanoyl]amino]-3-methylbutyl]boronic acid) which, like bortezomib, are reversible boronic acid proteasome inhibitors.

Bortezomib is presently marketed under the registered name Velcade®, sold as a powder for solution for intravenous or subcutaneous injection.

Ixazomib is marketed as an oral prescription medicine under the registered name Ninlaro®, and is generally used in combination with Revlimid® (lenalidomide) and dexamethasone, in patients suffering from multiple myeloma who have received at least one prior treatment (i.e. as a second-line treatment).

Carfilzomib is marketed as an injection prescription medicine under the registered name Kyprolis®. It has been used in the setting of relapsed and/or refractory MM, as a single agent with or without dexamethasone, and in combination with lenalidomide.

A further PI is marizomib ((1R,4R,5S)-4-(2-chloroethyl)-1-[(S)-[(1S)-cyclohex-2-en-1-yl]-hydroxymethyl]-5-methyl-6-oxa-2-azabicyclo[3.2.0]heptane-3,7-dione) which is a β-lactone, presently undergoing preclinical studies in hematological cancers, such as multiple myeloma, Waldenstrom's macroglobulinemia, Burkitt's lymphoma, chronic lymphocytic leukemia, acute lymphocytic leukemia, mantle cell lymphoma, as well as in solid tumors, such as colon cancer, pancreatic cancer, prostate cancer, melanoma, glioma, squamous cell carcinoma, non-small cell lung carcinoma, and renal carcinoma.

Immunomodulatory drugs have also been developed for use in therapy. For example, thalidomide (2-(2,6-dioxopiperidin-3-yl)isoindoline-1,3-dione) and its two analogs lenalidomide (3-(4-amino-1-oxoisoindolin-2-yl)piperidine-2,6-dione) and pomalidomide (4-amino-2-(2,6-dioxopiperidin-3-yl)isoindoline-1,3-dione) are well-known immunomodulatory drugs that have been approved for the treatment of multiple myeloma.

Thalidomide is used as a first-line treatment in multiple myeloma in combination with e.g. dexamethasone, as well as being used e.g. in the treatment of graft versus host disease and aphthous stomatitis in children.

Lenalidomide is marketed as an oral medication under various trade names, e.g. Revlimid®. Lenalidomide is used in combination with dexamethasone in patients with multiple myeloma who have received at least one prior therapy, and also as a standalone maintenance therapy for patients with multiple myeloma following autologous stem cell transplant. Additionally, lenalidomide is approved for use in the treatment of mantle cell lymphoma (MCL) in patients whose disease has relapsed or progressed after two prior therapies, one of which included bortezomib. Lenalidomide is undergoing clinical trial as a treatment for Hodgkin's lymphoma, non-Hodgkin's lymphoma, chronic lymphocytic leukemia and solid tumor cancers, such as carcinoma of the pancreas.

Pomalidomide, is an orally bioavailable derivative of thalidomide which has been approved for the treatment of relapsed and refractory multiple myeloma, for which it has been used in combination with bortezomib and dexamethasone.

The treatment arsenal for multiple myeloma also includes antibodies, in particular monoclonal antibodies, such as the monoclonal CD38 antibody daratumumab, which has been used in patients with newly diagnosed multiple myeloma who cannot receive autologous stem cell transplant. Daratumumab has been used in combination with bortezomib, melphalan and prednisone. Daratumumab has also been used as a second-line treatment of multiple myeloma, in combination with lenalidomide and dexamethasone or bortezomib and dexamethasone, and as a third-line treatment in combination with pomalidomide and dexamethasone. In patients who have received at least three prior medicines to treat multiple myeloma, including a proteasome inhibitor and an immunomodulatory imide, or that did not respond to a proteasome inhibitor and an immunomodulatory imide, daratumumab has been used as monotherapy.

A further antibody that has been approved for the treatment of multiple myeloma is elotuzumab, a SLAMF7-directed (CD 319) immunostimulatory monoclonal antibody, used as a second-line treatment in combination with lenalidomide and dexamethasone.

Multiple myeloma is not a curable disease, the disease will eventually, but inevitably, become refractory to the on-going treatment, and in the best-case scenario, a new treatment option may then be found to combat disease progression. Clearly, there is an urgent need for further therapies to provide new options in disease control.

SUMMARY OF THE INVENTION

The present invention is based on the discovery of a surprisingly positive effect, in some cases even synergistic effect, obtained in the treatment of multiple myeloma by the combined use of tasquinimod and at least one further compound selected from (i) a proteasome inhibitor, (ii) an immunomodulatory imide, and (iii) an antibody.

A first aspect, therefore, is a combination comprising tasquinimod, or a pharmaceutically acceptable salt thereof, and at least one further compound selected from (i) a proteasome inhibitor, (ii) an immunomodulatory imide, and (iii) an antibody.

A further aspect is a combination as defined herein above, for use in therapy.

Further disclosed herein is a combination comprising tasquinimod, or a pharmaceutically acceptable salt thereof, and at least one further compound selected from (i) a proteasome inhibitor, (ii) an immunomodulatory imide, and (iii) an antibody, for use in the treatment of cancer, e.g. a hematologic cancer, such as in particular multiple myeloma.

Further disclosed herein is a pharmaceutical composition comprising tasquinimod, or a pharmaceutically acceptable salt thereof, and at least one further compound selected from (i) a proteasome inhibitor, (ii) an immunomodulatory imide, and (iii) an antibody.

Further disclosed herein is a kit comprising tasquinimod and a package insert comprising instructions for using tasquinimod in combination with at least one further compound selected from (i) a proteasome inhibitor, (ii) an immunomodulatory imide, and (iii) an antibody, for the treatment of cancer, in particular a hematologic cancer, such as multiple myeloma.

In some embodiments, the kit additionally comprises one or more of further compounds selected from (i) a proteasome inhibitor, (ii) an immunomodulatory imide, and (iii) an antibody.

A further aspect is tasquinimod or a pharmaceutically acceptable salt thereof, for use in the treatment of cancer, e.g. a hematologic cancer, such as multiple myeloma, wherein the treatment further comprises administration of at least one further compound selected from (i) a proteasome inhibitor, (ii) an immunomodulatory imide, and (iii) an antibody.

In some embodiments, the treatment comprises administration to an individual, of an amount of from 0.001 mg to 0.2 mg of tasquinimod/kg of body weight per day, or of a corresponding amount of a pharmaceutically acceptable salt thereof, in combination with administration of the at least one further compound, simultaneously, sequentially, or separately.

Preferably, the administration of tasquinimod, or a pharmaceutically acceptable salt thereof, is oral, but it also may be e.g. rectal, or parenteral, e.g. by injection, such as subcutaneous, intramuscular or intravenous injection. The mode of administration of the at least one further compound will depend on the particular further compound selected, and may be enteral, e.g. oral, or parenteral, e.g. by injection, e.g. subcutaneous, intramuscular or intravenous injection.

In some embodiments, the treatment further comprises radiation therapy.

In some embodiments, the treatment further comprises stem cell transplantation, e.g. autologous stem cell transplantation.

Further disclosed herein is the use of tasquinimod or a pharmaceutically acceptable salt thereof, in the manufacture of a medicament for use in combination with at least one further compound selected from (i) a proteasome inhibitor, (ii) an immunomodulatory imide, and (iii) an antibody, for the treatment of a hematologic cancer, such as multiple myeloma.

Further disclosed herein is the use of tasquinimod or a pharmaceutically acceptable salt thereof, and at least one further compound selected from (i) a proteasome inhibitor, (ii) an immunomodulatory imide, and (iii) an antibody, in the manufacture of a medicament for the treatment of a hematologic cancer, such as multiple myeloma.

Further disclosed herein is the use of a compound selected from (i) a proteasome inhibitor, (ii) an immunomodulatory imide, and (iii) an antibody, in the manufacture of a medicament for use in combination with tasquinimod, or a pharmaceutically acceptable salt thereof, for the treatment of a hematologic cancer, such as multiple myeloma.

Further disclosed herein is a method of treatment of cancer, in particular a hematologic cancer, such as multiple myeloma, comprising administering tasquinimod or a pharmaceutically acceptable salt thereof to an individual, in need of such treatment, in combination with at least one further compound selected from (i) a proteasome inhibitor, (ii) an immunomodulatory imide, and (iii) an antibody.

In some embodiments, the at least one further compound is selected from (i) a proteasome inhibitor, and (ii) an immunomodulatory imide. In some embodiments, the at least one further compound is selected from (i) a proteasome inhibitor, and (iii) an antibody.

In some other embodiments, the at least one further compound is a proteasome inhibitor. The proteasome inhibitor e.g. may be a peptide boronic acid or a pharmaceutically acceptable salt thereof, such as bortezomib, ixazomib, or delanzomib; a peptide epoxyketone, such as carfilzomib or oprozomib; or a β lactone, such as marizomib. In some embodiments, the proteasome inhibitor is a peptide boronic acid or a peptide epoxyketone. In some embodiments, the proteasome inhibitor is a peptide boronic acid, e.g. bortezomib.

The immunomodulatory imide e.g. may be selected from thalidomide, lenalidomide and pomalidomide.

The antibody e.g. may be a CD38 antibody such as daratumumab or ixatuximab, or a SLAMF7-directed (CD 319) immunostimulatory antibody, such as elotuzumab.

In some embodiments, the combination also comprises a corticosteroid, e.g. dexamethasone or prednisone.

DETAILED DESCRIPTION OF THE INVENTION

Figure 1:
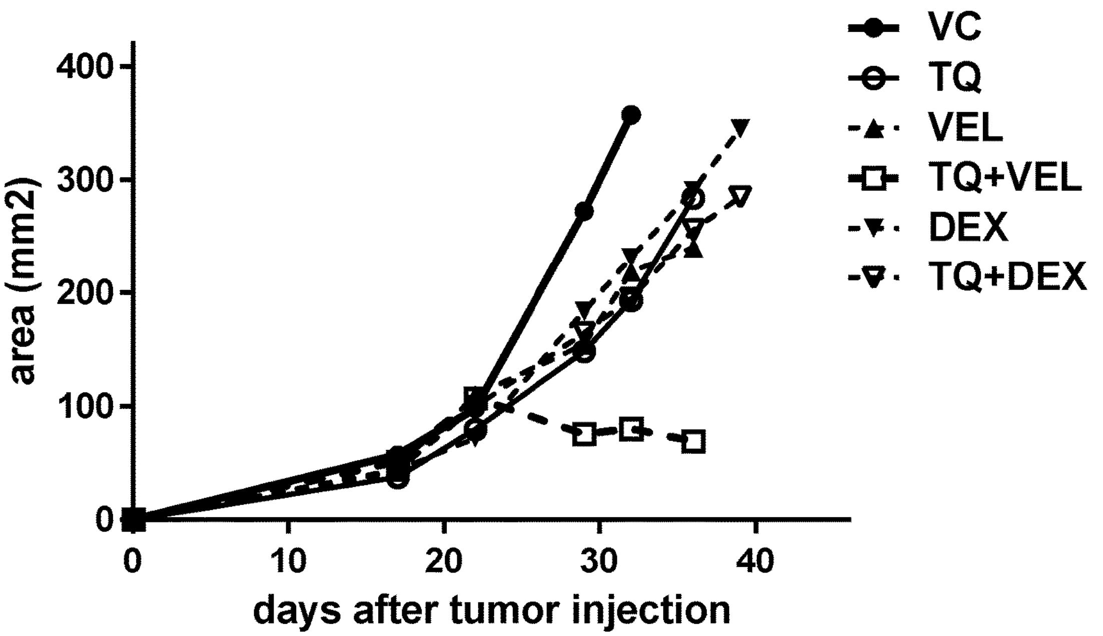
FIG. 1 is a graph showing the tumour area in mice in the human H929 human xenograft model as a function of days of treatment with a combination of tasquinimod and bortezomib (TQ+VEL) and, for comparison, with vehicle only (VC), tasquinimod only (TQ), bortezomib only (VEL), or with dexamethasone (DEX) or tasquinimod and dexamethasone (TQ+DEX).

Unless defined otherwise or clearly indicated by context, all technical and scientific terms and abbreviations used herein have the same meaning as commonly understood by one of ordinary skill in the field of art to which this disclosure belongs. However, definitions of some of the terms used herein will be given herein below.

It should be noted that there are several synonymous terms designating the disease "multiple myeloma", including Kahler disease, myeloma, myelomatosis, plasma cell dyscrasia and plasma cell myeloma. For the purpose of the present invention, these terms are all considered to be interchangeable with the term multiple myeloma.

"Optional" or "optionally" means that the subsequently described event or circumstance may but need not occur, and that the description includes instances where the event or circumstance occurs and instances in which it does not.

"Pharmaceutically acceptable" means that which is useful in preparing a pharmaceutical composition that is generally safe, non-toxic, and neither biologically nor otherwise undesirable and includes that which is acceptable for veterinary use as well as human pharmaceutical use.

Examples of pharmaceutically acceptable salts include salts with (as counter ion) an alkali metal ion, e.g. $Li^+$, $Na^+$ or $K^+$, or with an alkaline earth metal ion, e.g. $Mg^{2+}$ or $Ca^{2+}$, or with any other pharmaceutically acceptable metal ion, e.g. $Zn^{2+}$ or $Al^{3+}$; or pharmaceutically acceptable salts formed with organic bases, such as diethanolamine, ethanolamine, N-methylglucamine, triethanolamine or tromethamine.

Reference to "tasquinimod" as made herein should be construed as a reference to the free base or a pharmaceutically acceptable salt or solvate thereof, unless otherwise specified or apparent from the context.

The term "proteasome inhibitor" (which may also be referred to as "PI") as used herein refers to a compound that blocks the action of proteasomes, i.e. cellular complexes that break down proteins, such as for example the p53 protein.

The term "immunomodulatory imide" (which may also be referred to as immunomodulatory imide drug, or IMiD) as used herein refers to a compound having at least one imide functionality and that is capable of modifying the immune response or the functioning of the immune system (as by the stimulation of antibody formation or the inhibition of white blood cell activity), in particular the term refers to thalidomide or a compound which is a structural and functional analog of thalidomide and that has immunomodulatory properties, e.g. lenalidomide or pomalidomide. An imide functionality is a functional group containing two carbonyl functions attached to one and the same nitrogen atom, i.e. a functional group that may be represented by the structural formula

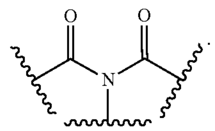 [SMILES: *C(=O)N(*)C(*)=O]

"Therapeutically effective amount" means an amount of a therapeutically active ingredient, e.g. tasquinimod or a pharmaceutically salt thereof, that, when administered in combination with a further compound as defined herein, for treating a disease state (e.g. MM) of a subject, is sufficient to effect such treatment for the disease state. The "therapeutically effective amount" will vary depending on e.g. the age and relative health of the treated subject, the state of progression of the disease, the route and form of administration, the particular combination of tasquinimod and further compound(s) selected, etc.

As used herein the terms "treatment" or "treating" is an approach for obtaining beneficial or desired results including clinical results. Beneficial or desired clinical results can include, but are not limited to, alleviation or amelioration of one or more symptoms of the treated disease (e.g MM), diminishment of extent of the disease, stabilization (i.e., not worsening) of the state of the disease, preventing spread of the disease, delay or slowing of progression of the disease, amelioration or palliation of the disease state, and remission (whether partial or total), whether detectable or undetectable. The term can also mean prolonging survival as compared to expected survival without the treatment.

Common symptoms of MM are bone pain due to lytic bone disease, weakness and fatigue due to anemia, weight loss, confusion, excessive thirst, constipation due to hypercalcemia, kidney problems, infections due to non-functioning immunoglobulins. More uncommon symptoms comprise accumulation of plasma cells in purplish lumps visible underneath the skin, so called extramedullary plasmacytomas.

The term "relapsing multiple myeloma" (or "relapsed multiple myeloma") refers to worsening of symptoms of multiple myeloma in an individual, after a period of remission, e.g. after a period of treatment of the individual, leading to previous improvement of symptoms.

The term "refractory multiple myeloma" refers to a condition where the multiple myeloma does not respond to the given therapy, i.e. a condition where a new mode of treatment or a new combination of drugs may become necessary.

The term "CD38 antibody" as used herein (also termed anti-CD38 antibody) is an antibody targeting the CD38 (cluster of differentiation 38), present at the surface of various immune cells (white blood cells), including CD4+, CD8+, B lymphocytes and natural killer cells.

The term "SLAMF7 (CD 319) antibody" (or (anti-SLAMF7 antibody) refers to an antibody targeting the plasma cell surface antigen SLAMF7 (also referred to as SLAM F7, 19A, CD319, CRACC, CS1, or SLAM family member 7)

The term "individual" (or "subject", which may be used synonymously herein) as used herein refers generally to a mammal, which may be a human or any mammalian animal, e.g. a primate, a farm animal, a pet animal, or a laboratory animal. Preferably, the individual is a human.

The individual that may suitably be treated according to the present invention may be one suffering from MM, or one at (increased) risk of developing MM, or one no longer responding to the therapy given. There are patients suffering from certain other conditions that have an increased risk of developing MM. Such conditions are monoclonal gammopathy of uncertain significance (MGUS) and solitary plasmacytoma. In fact, these conditions may even be early forms of MM. Therefore, in some embodiments, the term MM also includes a condition selected from monoclonal gammopathy of uncertain significance (MGUS) and solitary plasmacytoma.

In some other embodiments, the MM is smoldering multiple myeloma (SMM), an early precursor of MM that can be diagnosed by measuring certain proteins in the blood and urine of the patient. Thus, SMM generally is diagnosed in persons who meet the following criteria: (1) serum monoclonal (M) protein g/dL and/or 10 to 60 percent bone marrow clonal plasma cells; and (2) absence of lytic lesions, anemia, hypercalcemia, and renal insufficiency (end-organ damage) that can be attributed to the plasma cell proliferative disorder and the absence of biomarkers associated with near inevitable progression to end-organ damage (60 percent clonal plasma cells in the marrow; involved/uninvolved free light chain ratio of 100 or more; or more than one focal bone lesion on magnetic resonance imaging).

SMM is distinguished from multiple myeloma (MM) based on the lack of end-organ damage; it is distinguished from monoclonal gammopathy of undetermined significance (MGUS) based on the size of the M protein and the percent plasma cells in the bone marrow.

Tasquinimod has the Structural Formula

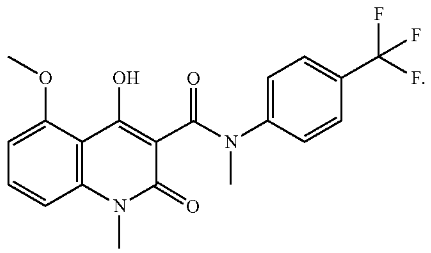 [SMILES: COc1cccc2c1c(O)c(C(=O)N(C)c1ccc(C(F)(F)F)cc1)c(=O)n2C]

As mentioned herein above, tasquinimod, pharmaceutically acceptable salts thereof, deuterated forms thereof, crystalline salts thereof, and pharmaceutical compositions containing tasquinimod or its salt, as well as methods for preparing tasquinimod, its salts, deuterated forms and pharmaceutical compositions containing tasquinimod and tasquinimod salts have been described in WO 99/55678, WO 00/03991, WO 03/106424, WO 2012/004338 and WO 2012/175541 (vide supra), which documents are hereby incorporated by reference in their entireties into the present application.

In some embodiments, any reference to tasquinimod also encompasses the deuterated form of thereof. As mentioned herein above, a deuterated form of tasquinimod is described in WO 2012/175541. In some embodiments, thus, tasquinimod has a deuterium enrichment in the amide-N methyl of at least 70%, more preferably at least 90%. In some other embodiments, tasquinimod is non-deuterated, having a deuterium content corresponding to the natural abundance of deuterium.

Any proteasome inhibitor (PI) is contemplated as useful for the purpose of the present invention. For example, the PI may be a peptide boronic acid or a pharmaceutically acceptable salt thereof (a peptide boronate), such as bortezomib, ixazomib, or delanzomib; a peptide epoxyketone, such as carfilzomib or oprozomib; or a β lactone, such as marizomib.

The name, type and structural formula of some proteasome inhibitors that are contemplated as useful herein are shown in Table 1.

TABLE 1

| Name | Type | Structural formula |
|---|---|---|
| bortezomib | peptide boronic acid | 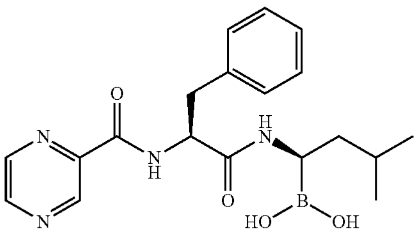 [SMILES: CC(C)C[C@H](NC(=O)[C@H](Cc1ccccc1)NC(=O)c1cnccn1)B(O)O] |
| ixazomib | peptide boronic acid | 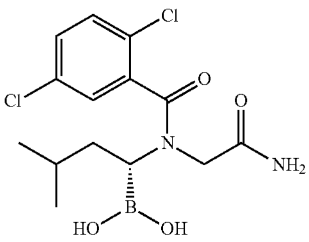 [SMILES: CC(C)C[C@@H](B(O)O)N(CC(N)=O)C(=O)c1cc(Cl)ccc1Cl] |

TABLE 1-continued

| Name | Type | Structural formula |
|---|---|---|
| delanzomib | peptide boronic acid | 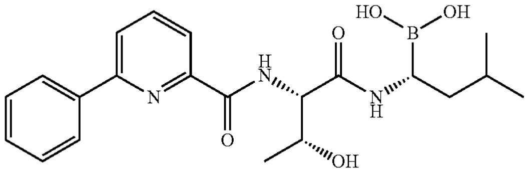 [SMILES: CC(C)C[C@H](NC(=O)[C@@H](NC(=O)c1cccc(-c2ccccc2)n1)[C@@H](C)O)B(O)O] |
| carfilzomib | peptide epoxyketone | 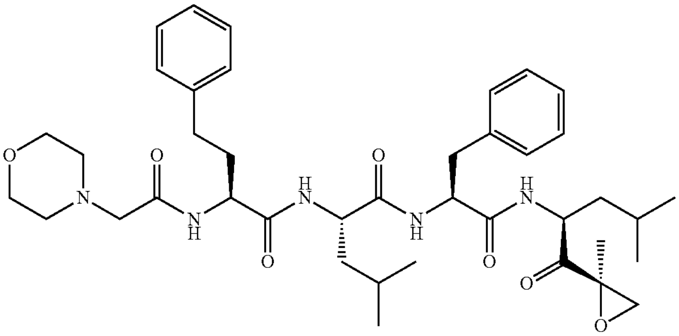 [SMILES: CC(C)C[C@H](NC(=O)[C@H](CCc1ccccc1)NC(=O)CN1CCOCC1)C(=O)N[C@@H](Cc1ccccc1)C(=O)N[C@@H](CC(C)C)C(=O)[C@@]1(C)CO1] |
| oprozomib | peptide epoxyketone | 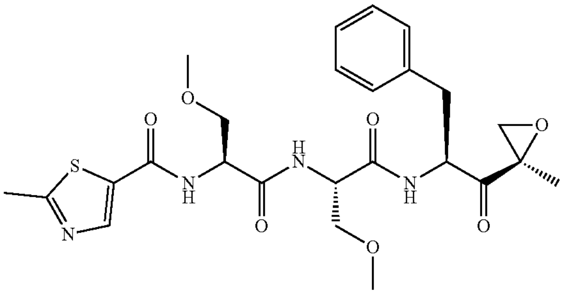 |
| marizomib | β lactone | 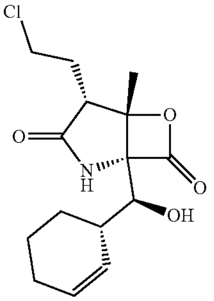 [SMILES: C[C@@]12OC(=O)[C@]1([C@@H](O)[C@@H]1C=CCCC1)NC(=O)[C@@H]2CCCl] |

In some embodiments, the PI is selected from a peptide boronic acid and a peptide epoxyketone. In some embodiments, the PI is selected from a peptide boronic acid and a β lactone. In some embodiments, the PI is selected from a peptide epoxyketone and a β lactone. In some embodiments, the PI is a peptide boronic acid. In some embodiments, the PI is a peptide epoxyketone. In some embodiments, the PI is β lactone.

In some embodiments, the peptide boronic acid is selected from bortezomib, ixazomib, and delanzomib; e.g. from bortezomib and ixazomib. In some embodiments, the peptide boronic acid is bortezomib. In some embodiments, the peptide boronic acid is ixazomib. In some embodiments, the peptide boronic acid is delanzomib.

In some embodiments, the peptide epoxyketone, is selected from carfilzomib and oprozomib. In some embodiments, the peptide epoxyketone, is carfilzomib. In some embodiments, the peptide epoxyketone is oprozomib. In some embodiments, the β lactone is marizomib.

The immunomodulatory imide for combined use with tasquinimod preferably is selected from thalidomide, lenalidomide and pomalidomide, the structural formulas of which are illustrated in Table 2.

TABLE 2

| Name | Structural formula |
|---|---|
| thalidomide | 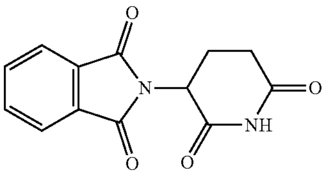 [SMILES: O=C1CCC(N2C(=O)c3ccccc3C2=O)C(=O)N1] |

TABLE 2-continued

| Name | Structural formula |
|---|---|
| lenalidomide | 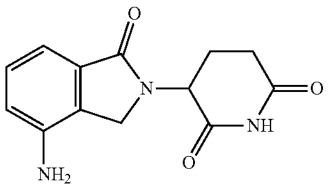 [SMILES: Nc1cccc2c1CN(C1CCC(=O)NC1=O)C2=O] |
| pomalidomide | 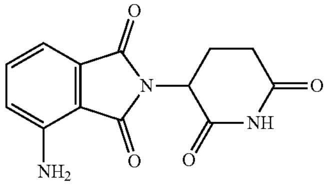 [SMILES: Nc1cccc2c1C(=O)N(C1CCC(=O)NC1=O)C2=O] |

In some embodiments, the IMiD is selected from thalidomide and lenalidomide. In some embodiments, the IMiD is selected from thalidomide and pomalidomide. In some embodiments, the IMiD is selected from lenalidomide and pomalidomide. In some embodiments, the IMiD is lenalidomide. In some embodiments, the IMiD is pomalidomide. In some embodiments, the IMiD is thalidomide.

An "antibody" for use herein may be a natural or conventional antibody in which two heavy chains are linked to each other by disulfide bonds and each heavy chain is linked to a light chain by a disulfide bond. There are two types of light chain, lambda (l) and kappa (κ). There are five main heavy chain classes (or isotopes) which determine the functional activity of an antibody molecule: IgA, IgD, IgE, IgG, and IgM, and, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2. Each chain contains distinct sequence domains. The light chain includes two domains or regions, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated CDR1-L, CDR2-L, CDR3-L and CDR1-H, CDR2-H, CDR3-H, respectively. A conventional antibody antigen-binding site, therefore, includes six CDRs, comprising the CDR set from each of a heavy and a light chain V region.

"Framework Regions" (FRs) refer to amino acid sequences interposed between CDRs, i.e. to those portions of immunoglobulin light and heavy chain variable regions that are relatively conserved among different immunoglobulins in a single species. The light and heavy chains of an immunoglobulin each have four FRs, designated FR1-L, FR2-L, FR3-L, FR4-L, and FR1-H, FR2-H, FR3-H, FR4-H, respectively.

As used herein, a "human framework region" is a framework region that is substantially identical (about 85%, or more, in particular 90%, 95%, 97%, 99% or 100%) to the framework region of a naturally occurring human antibody.

As used herein, the term "antibody" denotes conventional antibodies and fragments thereof, as well as single domain antibodies and fragments thereof, in particular variable heavy chain of single domain antibodies, and chimeric, humanized, bispecific or multispecific antibodies.

As used herein, antibody or immunoglobulin also includes "single domain antibodies" which have been more recently described and which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit and bovine. Single domain antibodies may be naturally occurring single domain antibodies known as heavy chain antibody devoid of light chains. In particular, Camelidae species, for example camel, dromedary, llama, alpaca and guanaco, produce heavy chain antibodies naturally devoid of light chain. Camelid heavy chain antibodies also lack the CH1 domain.

The variable heavy chain of these single domain antibodies devoid of light chains are known in the art as "VHH" or "nanobody". Similar to conventional VH domains, VHHs contain four FRs and three CDRs. Nanobodies have advantages over conventional antibodies: they are about ten times smaller than IgG molecules, and as a consequence properly folded functional nanobodies can be produced by in vitro expression while achieving high yield. Furthermore, nanobodies are very stable, and resistant to the action of proteases. The properties and production of nanobodies have been reviewed by Harmsen and De Haard H J (Appl. Microbiol. Biotechnol. 2007 November; 77(1): 13-22).

The antibody of the invention may be a polyclonal antibody or a monoclonal antibody. Said monoclonal antibody may be humanized. In another example the antibody may be a fragment selected from the group consisting of Fv, Fab, F(ab')2, Fab', dsFv, (dsFv)2, scFv, sc(Fv)2, diabodies and VHH.

The term "monoclonal antibody" or "mAb" as used herein refers to an antibody molecule of a single amino acid composition that is directed against a specific antigen, and is not to be construed as requiring production of the antibody by any particular method. A monoclonal antibody may be produced by a single clone of B cells or hybridoma, but may also be recombinant, i.e. produced by protein engineering.

The term "chimeric antibody" refers to an engineered antibody which in its broadest sense contains one or more regions from one antibody and one or more regions from one or more other antibody(ies). In particular, a chimeric antibody comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens. In an embodiment, a chimeric antibody has variable domains of mouse origin and constant domains of human origin.

The term "humanized antibody" refers to an antibody which is initially wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains. In an embodiment, a humanized antibody has constant domains of human origin.

"Fragments" of antibodies comprise a portion of an intact antibody, in particular the antigen binding region or variable region of the intact antibody. Examples of antibody fragments include Fv, Fab, F(ab')2, Fab', dsFv, (dsFv)2, scFv, sc(Fv)2, diabodies, bispecific and multispecific antibodies formed from antibody fragments. A fragment of an antibody may also be a single domain antibody, such as a heavy chain antibody or VHH.

The term "Fab" denotes an antibody fragment having a molecular weight of about 50,000 Da and antigen binding activity, in which about a half of the N-terminal side of H chain and the entire L chain, among fragments obtained by treating IgG with a protease, papaine, are bound together through a disulfide bond.

The term "F(ab')2" refers to an antibody fragment having a molecular weight of about 100,000 Da and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 Da and antigen binding activity, which is obtained by cutting a disulfide bond of the hinge region of the F(ab')2.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent $sc(Fv)_2$. "dsFv" is a VH::VL heterodimer stabilised by a disulphide bond.

The term "(dsFv)2" denotes two dsFv coupled by a peptide linker.

The term "bispecific antibody" or "BsAb" denotes an antibody which combines the antigen-binding sites of two antibodies within a single molecule. Thus, BsAbs are able to bind two different antigens simultaneously. Genetic engineering has been used with increasing frequency to design, modify, and produce antibodies or antibody derivatives with a desired set of binding properties and effector functions as described for instance in EP 2 050 764 A1.

The term "multispecific antibody" denotes an antibody which combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

Typically, antibodies are prepared according to conventional methodology. Monoclonal antibodies may be generated using the method of Kohler and Milstein (Nature, 256:495, 1975).

To prepare monoclonal antibodies useful in the invention, a mouse or other appropriate host animal is immunized at suitable intervals (e.g., twice-weekly, weekly, twice-monthly or monthly) with the relevant antigenic forms. The animal may be administered a final "boost" of antigen within one week of sacrifice. It is often desirable to use an immunologic adjuvant during immunization. Suitable immunologic adjuvants include Freund's complete adjuvant, Freund's incomplete adjuvant, alum, Ribi adjuvant, Hunter's Titermax, saponin adjuvants such as QS21 or Quil A, or CpG-containing immunostimulatory oligonucleotides. Other suitable adjuvants are well-known in the field. The animals may be immunized by subcutaneous, intraperitoneal, intramuscular, intravenous, intranasal or other routes. A given animal may be immunized with multiple forms of the antigen by multiple routes.

This invention provides in certain embodiments compositions and methods that include humanized forms of antibodies. Methods of humanization include, but are not limited to, those described in U.S. Pat. Nos. 4,816,567, 5,225,539, 5,585,089, 5,693,761, 5,693,762 and 5,859,205, which are hereby incorporated by reference. The above U.S. Pat. Nos. 5,585,089 and 5,693,761, and WO 90/07861 also propose four possible criteria which may be used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three-dimensional model of the antibody and is predicted to be capable of interacting with the CDRs. The above methods are merely illustrative of some of the methods that one skilled in the art could employ to make humanized antibodies. One of ordinary skill in the art will be familiar with other methods for antibody humanization.

In one embodiment of the humanized forms of the antibodies, some, most or all of the amino acids outside the CDR regions have been replaced with amino acids from human immunoglobulin molecules but where some, most or all amino acids within one or more CDR regions are unchanged. Small additions, deletions, insertions, substitutions or modifications of amino acids are permissible as long as they would not abrogate the ability of the antibody to bind a given antigen. Suitable human immunoglobulin molecules would include IgGI, IgG2, IgG3, IgG4, IgA and IgM molecules. A "humanized" antibody retains a similar antigenic specificity as the original antibody. However, using certain methods of humanization, the affinity and/or specificity of binding of the antibody may be increased using methods of "directed evolution", as described by Wu et al., *I. Mol. Biol.* 294:151, 1999, the contents of which are incorporated herein by reference.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals will result in the production of fully human antibodies to the antigen of interest. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (KAMA) responses when administered to humans.

In vitro methods also exist for producing human antibodies. These include phage display technology (U.S. Pat. Nos. 5,565,332 and 5,573,905) and in vitro stimulation of human B cells (U.S. Pat. Nos. 5,229,275 and 5,567,610). The contents of these patents are incorporated herein by reference.

In some embodiments, the antibody of the invention is modified to reduce or inhibit the ability of the antibody to mediate antibody dependent cellular cytotoxicity (ADCC) and/or complement dependent cytotoxicity (CDC) functionality (i.e. an antibody with reduced Fc-effector function"). In particular, the antibodies of the present invention have no Fc portion or have an Fc portion that does not bind FcγRI and C1q. In one embodiment, the Fc portion of the antibody does not bind FcγRI, C1q, or FcγRIII. Antibodies with such functionality, in general, are known. There are native such antibodies, such as antibodies with an IgG4 Fc region. There also are antibodies with Fc portions genetically or chemically altered to eliminate the Antibody dependent cell cytotoxicity (ADCC) and/or complement dependent cytotoxicity (CDC) functionality.

In some embodiments, the antibody is a monoclonal antibody. In some embodiments, the antibody is a CD38 antibody, e.g. a monoclonal CD38 antibody, such as daratumumab or ixatuximab. In some embodiments, the antibody is daratumumab or ixatuximab. In some embodiments, the antibody is daratumumab. In some embodiments, the antibody is ixatuximab.

In some other embodiments, the antibody is a (preferably monoclonal) SLAMF7 (CD 319) antibody, e.g. a monoclonal SLAMF7-directed (CD 319) immunostimulatory antibody, such as elotuzumab.

In some embodiments, the antibody is selected from daratumumab, ixatuximab, and elotuzumab; e.g. from daratumumab and elotuzumab, or from ixatuximab and elotuzumab.

The antibody may be administered by intravenous (IV) infusion, or by injection, e.g. subcutaneous injection. For example, daratumumab has been approved for subcutaneous injection, and therefore, in some embodiments the antibody is administered by subcutaneous injection.

The combination disclosed herein, of tasquinimod or a pharmaceutically acceptable salt thereof, and the at least one further compound as defined herein, is useful in therapy, in particular for the treatment of cancer, such as a hematologic cancer, e.g. multiple myeloma, including relapsed and/or refractory multiple myeloma.

By "combination" as used herein is meant that tasquinimod and at least one further compound (herein below also referred to as "the further compound") may be administered simultaneously in one and the same formulation or in separate formulations. The combination of tasquinimod and the further compound includes administration of each compound separately, e.g. sequentially or at different time points. In the case of separate administration it is contemplated that the time period elapsing between administering tasquinimod and the further compound preferably is enough short for the two compounds to have therapeutic activity in the treated individual that is overlapping in time. In some embodiments, tasquinimod and the further compound are administered essentially at the same time, e.g. simultaneously (concomitantly) or sequentially.

As will be shown herein, in some embodiments, the combined use of tasquinimod and a further compound as defined herein very advantageously may provide a synergistic therapeutic effect, i.e. a more than additive effect.

It is contemplated that tasquinimod and the further compound as defined herein may be used in a molar ratio of tasquinimod to further compound of from about 1:100 to about 100:1, e.g. from 1:50 to 50:1, or from 1:20 to 20:1, e.g. 1:10 to 10:1, or 1:5 to 5:1, or 1:2 to 2:1, though higher or lower ratios may be applied depending on, in particular, the further compound used.

In some embodiments, the combination comprises tasquinimod, or a pharmaceutically acceptable salt thereof, and one further compound selected from (i) a proteasome inhibitor, such as bortezomib, ixazomib, delanzomib, carfilzomib, oprozomib; or marizomib;
(ii) an immunomodulatory imide, such as thalidomide, lenalidomide, or pomalidomide; and
(iii) an antibody, such as daratumumab, ixatuximab, or elotuzumab; e.g. daratumumab, or elotuzumab.

In some embodiments, the combination comprises tasquinimod, or a pharmaceutically acceptable salt thereof, and two further compounds, selected from (i) a proteasome inhibitor, (ii) an immunomodulatory imide, and (iii) an antibody.

In some embodiments, the combination comprises tasquinimod, or a pharmaceutically acceptable salt thereof, (i) a proteasome inhibitor, and at least one further compound, selected from (ii) an immunomodulatory imide, and (iii) an antibody.

In some embodiments, the combination comprises tasquinimod, or a pharmaceutically acceptable salt thereof, (i) a proteasome inhibitor, and (ii) an immunomodulatory imide.

In some embodiments, the combination comprises tasquinimod, or a pharmaceutically acceptable salt thereof, (i) a proteasome inhibitor, and (ii) an antibody.

In some embodiments, the combination comprises tasquinimod, or a pharmaceutically acceptable salt thereof, (i) an immunomodulatory imide, and at least one further compound, selected from (ii) a proteasome inhibitor, and (iii) an antibody.

In some embodiments, the combination further comprises a corticosteroid, e.g. prednisone or dexamethasone, in particular dexamethasone.

One aspect of the invention is a pharmaceutical composition comprising tasquinimod or a pharmaceutically acceptable salt thereof for use in the treatment of multiple myeloma, wherein the treatment also comprises administration of a further compound selected from (i) a proteasome inhibitor, (ii) an immunomodulatory imide, and (iii) an antibody as defined herein.

Also disclosed herein is a pharmaceutical composition comprising, as active ingredient, a combination of tasquinimod or a pharmaceutically acceptable salt thereof and a further compound selected from (i) a proteasome inhibitor, (ii) an immunomodulatory imide, and (iii) an antibody as defined herein, together with a pharmaceutically acceptable excipient, e.g. a carrier. In embodiments of such composition, the further compound is as specified herein above in connection with embodiments of the combination as defined herein.

The pharmaceutical composition may be suitable for enteral administration, such as rectal or oral administration, or for parenteral administration, to a mammal (especially a human), and comprises the active ingredient, in a therapeutically effective amount, optionally in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, and the mode of administration.

For enteral, e.g. oral, administration, the active ingredient may be formulated in a wide variety of dosage forms. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions, or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well-known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The active ingredient also may be administered parenterally, e.g. by injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion. Thus, for parenteral administration, the pharmaceutical compositions may be in the form of a sterile injectable or infusible preparation, for example, as a sterile aqueous or oleaginous suspension. This suspension may be formulated according to techniques known in the art using suitable dispersing or wetting agents (e.g., Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and chlorobutanol.

Conventional procedures for the selection and preparation of suitable pharmaceutical formulations are described, for example, in "Pharmaceutics—The Science of Dosage Form Design", M. B. Aulton, Churchill Livingstone, $2^{nd}$ ed. 2002 (ISBN 0443055173, 9780443055171). Suitable pharmaceutical excipients, e.g. carriers, and methods of preparing pharmaceutical dosage forms also are described in Remington's Pharmaceutical Sciences, Mack Publishing Company, a standard reference text in art of drug formulation.

The pharmaceutical composition may comprise from about 1% to about 95% active ingredient, by weight of the composition, wherein the remainder is comprised of at least one pharmaceutically acceptable excipient. In some embodiments, pharmaceutical composition comprises at least 5%, at least 10%, at least 15% or at least 20% of active ingredient. In some embodiments, the pharmaceutical composition comprises at most 90%, at most 85%, or at most 80%, of active ingredient. For example, in some embodiments, the pharmaceutical composition comprises from about 20% to about 90% of active ingredient, and at least one pharmaceutically acceptable excipient.

In general, the active ingredients used in the combination of the invention will be administered in a therapeutically effective amount by any of the accepted modes of administration for agents that serve similar utilities.

Several of the active ingredients contemplated for use in the inventive combination are commercially available and have been approved for use as medicaments. Thus, for example bortezomib is marketed as Velcade®, ixazomib is marketed as Ninlaro®, carfilzomib is marketed as Kyprolis®, lenalidomide is marketed as Revlimid®, pomalidomide is marketed as Pomalyst®, daratumumab is marketed as Darzalex®, ixatuximab is marketed as Sarclisa®, and elotuzumab is marketed as Empliciti®.

It is contemplated that such commercially available formulations may be useful in the various aspects of the present invention, including the use, the combination, the kit and the method. Likewise, administration modes and dosages as known and specified for such formulations are contemplated as useful in various aspects of the invention, optionally adapted in view of the advantageous effect obtained by the combination with tasquinimod or its pharmaceutically acceptable salt.

Thus, as noted herein above, combination therapies based on combinations of, in particular a proteasome inhibitor such as bortezomid, with dexamethasone and an immunomodulatory imide, such as lenalidomide, are already known. The treatment modes used in these combination methods may also be applied when practicing the method of the present invention, with suitable adaptations of e.g. modes of administration and dosages, in particular in view of the advantageous synergistic effect obtained which may provide for a possibility of reduced dosage. As is usual when determining a proper treatment regimen, the proper dosage will normally have to be determined by the treating physician, having regard to factors such as age, weight, condition, etc. of the treated patient.

In some embodiments, the inventive combination comprises administration of a proteasome inhibitor, e.g. bortezomib, given on an outpatient basis as a short intravenous infusion, e.g. on days 1, 4, 8, 11 of a 3-week cycle, for a total of up to 8 cycles. In some of these embodiments, the treatment further comprises administration of dexamethasone, e.g. on the day of the PI (e.g. bortezomib) administration and on the day after each PI administration, e.g. at a dose of about 20 mg.

While e.g. injection or rectal administration of the active ingredient may be contemplated if necessary, oral administration generally is considered the most convenient.

For example, the proteasome inhibitors ixazomib, oprozomib and delanzomib may be orally administered, as may also the immunomodulatory imides thalidomide, lenalidomide and pomalidomide; while the proteasome inhibitors bortezomib, carfilzomib, and marizomib as well as the antibodies are generally administered by injection or infusion. In some embodiments, the further compound is one capable of being orally administered, e.g. selected from ixazomib, oprozomib, delanzomib, thalidomide, lenalidomide and pomalidomide.

In embodiments where also a corticosteroid is administered, such corticosteroid e.g. may be dexamethasone or prednisone, which may be administered e.g. orally, e.g. as a tablet formulation.

In some embodiments, tasquinimod and the further compound will be administered in separate formulations, e.g. tasquinimod is administered as an oral preparation while the further compound is administered by injection. In such case, the above description of suitable pharmaceutical preparations may apply to each such formulation independently. For example, in some embodiments, tasquinimod is administered orally to an individual, and simultaneously, sequentially, or separately, further compound, is administered via injection or infusion.

In some embodiments, tasquinimod is administered orally to an individual, e.g. as a capsule or tablet, preceded by, followed by, or during injection or intravenous administration of a further compound as defined herein.

In some embodiments, administration of tasquinimod and administration of the one or more further compounds take place during the same 24-hour period, more preferably during the same 12-hour period, or during the same 6-hour period, or during the same 3-hour period, or during the same 2-hour period, or during the same 1-hour period, e.g. one directly following the other.

In some embodiments, administration of tasquinimod is performed daily, whereas administration of each one of the one or more further compounds is performed at a treatment schedule that may be the same as that of tasquinimod, or different, e.g. daily, or weekly, or at any other suitable interval.

Generally, a daily dosage of tasquinimod ranging from a minimum of 0.001 mg/kg body weight, or 0.002 mg/kg body weight or 0.005 mg/kg body weight or 0.01 mg/kg body weight, to a maximum of 0.2 mg/kg body weight, or 0.1 mg/kg body weight, or 0.05 mg/kg body weight, or 0.02 mg/kg body weight is contemplated.

In one embodiment, tasquinimod is administered in an amount of 0.05 to 0.15 mg/day, or 0.08 to 0.1 mg/day, e.g. 0.1 mg/day (or in a corresponding amount of pharmaceutically acceptable salt of tasquinimod).

In one embodiment, tasquinimod is administered in an amount of 0.1 to 0.3 mg/day, or 0.15 to 0.25 mg/day, e.g. 0.2 mg/day (or in a corresponding amount of pharmaceutically acceptable salt of tasquinimod).

In one embodiment, tasquinimod is administered in an amount of 0.1 to 1 mg/day, or 0.2 to 0.8 mg/day, e.g. 0.5 mg/day (or in a corresponding amount of pharmaceutically acceptable salt of tasquinimod).

In one embodiment, tasquinimod is administered in an amount of 0.2 to 1.5 mg/day, or 0.4 to 1.2 mg/day, e.g. 0.8 mg/day (or in a corresponding amount of pharmaceutically acceptable salt of tasquinimod).

In one embodiment, tasquinimod is administered in an amount of 0.5 to 2 mg/day, or 0.8 to 1.2 mg/day, e.g. 1 mg/day (or in a corresponding amount of pharmaceutically acceptable salt of tasquinimod).

In one embodiment, tasquinimod is administered in an amount of 0.8 to 3 mg/day, or 1 to 2.5 mg/day, e.g. 2 mg/day (or in a corresponding amount of pharmaceutically acceptable salt of tasquinimod).

In one embodiment, tasquinimod is administered in an amount of 1 to 6 mg/day, or 2 to 4 mg/day, e.g. 3 mg/day (or in a corresponding amount of pharmaceutically acceptable salt of tasquinimod).

In some embodiments, the dosage may be gradually adjusted to reach optimal results, so-called dosage titration. For example, dosage titration may comprise starting with a low daily dosage of e.g. 0.25 mg of the active ingredient as defined herein and maintaining this dose level for a period of 1 or 2 weeks. In case no significant side effects are encountered that may contraindicate raising the dose, the level may then be increased, e.g. to 0.5 mg/day for 1 or 2 weeks, after which period another increase may be contemplated, to reach a daily dosage of 1 mg, and so on. In such a method, if any significant side effects occur after an incremental increase of the dosage, the dosage may again be reduced to a previous level.

In some embodiments, if the combination includes a PI, the PI is administered once a week, e.g. at a dosage of 1-5 mg/week.

In some embodiments, if the combination includes an IMiD, the IMiD is administered daily, e.g. at a dosage of 10-40 mg/week.

In some embodiments, if the combination includes an antibody, the antibody is administered as an intravenous infusion of about 10-16 mg/kg body weight, following a scheme including weekly infusion during a period of e.g. up to 2 months, followed by infusion every two weeks for a period of e.g. up to about 3 months, and then followed by infusion about once a month for the entire treatment period.

In some embodiments, if the combination comprises an antibody, the antibody is administered by subcutaneous injection. For example, the combination includes daratumumab which is administered by subcutaneous injection.

In some embodiments, if the combination additionally includes a corticosteroid, such corticosteroid may be administered daily, e.g. orally at a daily dosage of from 0.5 to 10 mg.

Thus, generally, the active ingredients e.g. may be administrated on a daily basis, e.g. 1-3 times a day, or 1-2 times a day, such as once daily. In some embodiments, administration occurs on a less frequent basis, e.g. every two days, once a week etc., or by following established treatment cycles, over e.g. 3-6 weeks.

In some embodiments, tasquinimod and the further compound (i.e. any of the compounds (i) to (iii) as defined herein) are administered following different administration schedules and modes of administration. For example, tasquinimod is administered on a daily basis, and the further compound is administered on a less frequent basis, e.g. bi-daily, weekly, or bi-weekly.

In some embodiments, tasquinimod is administered as an oral preparation, e.g. as a capsule formulation, in combination with lenalidomide, also administered as an oral preparation, e.g. as a capsule formulation.

In some embodiments, tasquinimod is administered as an oral preparation, e.g. as a capsule formulation, in combination with pomalidomide, also administered as an oral preparation, e.g. as a capsule formulation.

In some embodiments, tasquinimod is administered as an oral preparation, e.g. as a capsule formulation, in combination with thalidomide, also administered as an oral preparation, e.g. as a capsule formulation.

In some embodiments, tasquinimod is administered as an oral preparation, e.g. as a capsule formulation, in combination with bortezomib, administered by intravenous injection.

In some embodiments, tasquinimod is administered as an oral preparation, e.g. as a capsule formulation, in combination with bortezomib, administered by subcutaneous injection.

In some embodiments, tasquinimod is administered as an oral preparation, e.g. as a capsule formulation, in combination with carfilzomib, administered by intravenous injection.

In some embodiments, tasquinimod is administered as an oral preparation, e.g. as a capsule formulation, in combination with ixazomib, also administered as an oral preparation, e.g. as a capsule formulation.

In some embodiments, tasquinimod is used in combination with more than one further therapeutically active compound selected from compounds (i) to (iii) as defined herein.

For example, in some embodiments, tasquinimod is used in combination with a PI and an IMiD; e.g. tasquinimod is used in combination with a PI selected from bortezomib, ixazomib, delanzomib, carfilzomib, oprozomib; and marizomib and with an IMiD selected from thalidomide, lenalidomide, and pomalidomide.

In some embodiments, tasquinimod is used in combination with bortezomib, and with an IMiD selected from thalidomide, lenalidomide, and pomalidomide. In some embodiments, tasquinimod is used in combination ixazomib and with an IMiD selected from thalidomide, lenalidomide, and pomalidomide. In some embodiments, tasquinimod is used in combination with delanzomib, and with an IMiD selected from thalidomide, lenalidomide, and pomalidomide. In some embodiments, tasquinimod is used in combination with carfilzomib, and with an IMiD selected from thalidomide, lenalidomide, and pomalidomide. In some embodiments, tasquinimod is used in combination with oprozomib; and with an IMiD selected from thalidomide, lenalidomide, and pomalidomide. In some embodiments, tasquinimod is used in combination with marizomib and with an IMiD selected from thalidomide, lenalidomide, and pomalidomide.

In some of the above embodiments, the IMiD is thalidomide. In some of the above embodiments, the IMiD is lenalidomide. In some of the above embodiments, the IMiD is pomalidomide.

In some of the above embodiments, the combination also comprises an antibody as defined herein, e.g. CD38 antibody or a SLAMF7-directed antibody, e.g. an antibody selected from daratumumab, ixatuximab, and elotuzumab.

In some embodiments, the combination further comprises administration of a corticosteroid. In some embodiments, the corticosteroid is dexamethasone. In some embodiments, the corticosteroid is prednisone.

The combination provided herein is useful in therapy, in particular in the treatment of cancer, more particularly hematologic cancer, such as multiple myeloma. The combination is considered particularly useful in the treatment of relapsing and/or refractory multiple myeloma. In some embodiments, the combination provided herein is for use in the treatment of relapsing multiple myeloma. In some embodiments, the combination provided herein is for use in the treatment of refractory multiple myeloma.

In some embodiments, the combination provided herein is for use as a first-line treatment of multiple myeloma, i.e. in the treatment of a patient not having received previous treatment of multiple myeloma.

In some embodiments, the combination provided herein is for use as a second-line treatment of multiple myeloma, i.e. in the treatment of a relapsing patient having previous received first-line treatment of multiple myeloma.

In some embodiments, the combination provided herein is for use as a third-line treatment of multiple myeloma, i.e. in the treatment of a patient having previously received second-line treatment of multiple myeloma.

It is contemplated that the combination herein may also be provided for fourth-line, fifth-line etc. treatment of multiple myeloma.

In some embodiments, the combination is used for the treatment of smoldering multiple myeloma. In some embodiments, the combination is used for the treatment of monoclonal gammopathy of uncertain significance (MGUS). In some further embodiments, the combination is used for the treatment of solitary plasmacytoma.

A further aspect disclosed herein is a kit comprising tasquinimod or a pharmaceutically acceptable salt thereof, and a package insert with instructions for using tasquinimod or its salt in combination with at least one further compound selected from (i) a proteasome inhibitor, (ii) an immunomodulatory imide, and (iii) an antibody, for the treatment of cancer, in particular hematologic cancer, such as multiple myeloma. In some embodiments, the kit further comprises instructions for using tasquinimod and the further compound with an additional formulation comprising a corticosteroid, e.g. dexamethasone or prednisone.

The particular embodiments of any such kit include features as defined in connection with the particular combinations, uses and pharmaceutical compositions described herein.

A further aspect disclosed herein is a method of treatment of cancer, in particular a hematologic cancer, such as multiple myeloma, comprising administering tasquinimod or a pharmaceutically acceptable salt thereof to an individual in need of such treatment, in combination with at least one further compound selected from (i) a proteasome inhibitor, (ii) an immunomodulatory imide, and (iii) an antibody. The particular embodiments of such method include features as defined in connection with the particular combinations, pharmaceutical combinations, uses and kits as described herein.

EXAMPLES

The invention is illustrated by the following non-limiting Examples.

Example 1

Use of Tasquinimod in Combination with Bortezomib

Human NCI-H929 (H929) multiple myeloma cells were inoculated subcutaneously in NSG mice. Tumour-bearing mice were treated with vehicle (VC), tasquinimod (TQ) 30 mg/kg ad lib in the drinking water starting when there were palpable tumors (i.e. day 18 after tumor inoculation); bortezomib (VEL), 0.5 mg/kg, i.v. every 4 days; dexamethasone (DEX), 10 mg/kg, i.p., 5 days on, 2 days off; or the combinations (TQ+DEX) and (TQ+VEL), and. Statistics: Two-way ANOVA; p-values VC vs TQ p=0.0009, VC vs VEL p=0.041, VC vs DEX p=0.0081, DEX vs DEX+TQ ns, TQ vs TQ+VEL p=0.0002, VEL vs VEL+TQ p=0.0361. The results are illustrated in FIG. 1. Both tasquinimod and bortezomib reduced the multiple myeloma tumor growth as compared to control mice when given as monotherapies in the H929 tumor model (FIG. 1). When combining tasquinimod with bortezomib, a synergistic improvement of the effect was recorded.

Example 2

Use of Tasquinimod in Combination with Lenalidomide

The effect of tasquinimod in combination with lenalidomide was studied in a human MM1.S model of multiple myeloma. The MM1.S cells were established from a patient with IgA myeloma with characteristics typical of human myeloma cells (Greenstein et al., Exp Hematol. 2003 April; 31(4):271-82). MM1.S model was established by subcutaneous inoculation of $5\times10^6$ MM1.S cells into NSG mice. Treatment with tasquinimod (TQ), 30 mg/kg/day in the drinking water; lenalidomide (LEN), 5 mg/kg via oral gavage, 5 consecutive days with 2 days breaks until the endpoint, or the combination of tasquinimod and lenalidomide (TQ+LEN), started when the tumors were measurable (day 14 after tumor cell injection). Tumor size was monitored using a caliper and tumor volume was calculated. Differences between groups were evaluated by using two-way ANOVA; p-values: TQ vs TQ+LEN p=0.0001, LEN vs LEN+TQ p=0.0183. The results are illustrated in FIG. 2.

Figure 2:
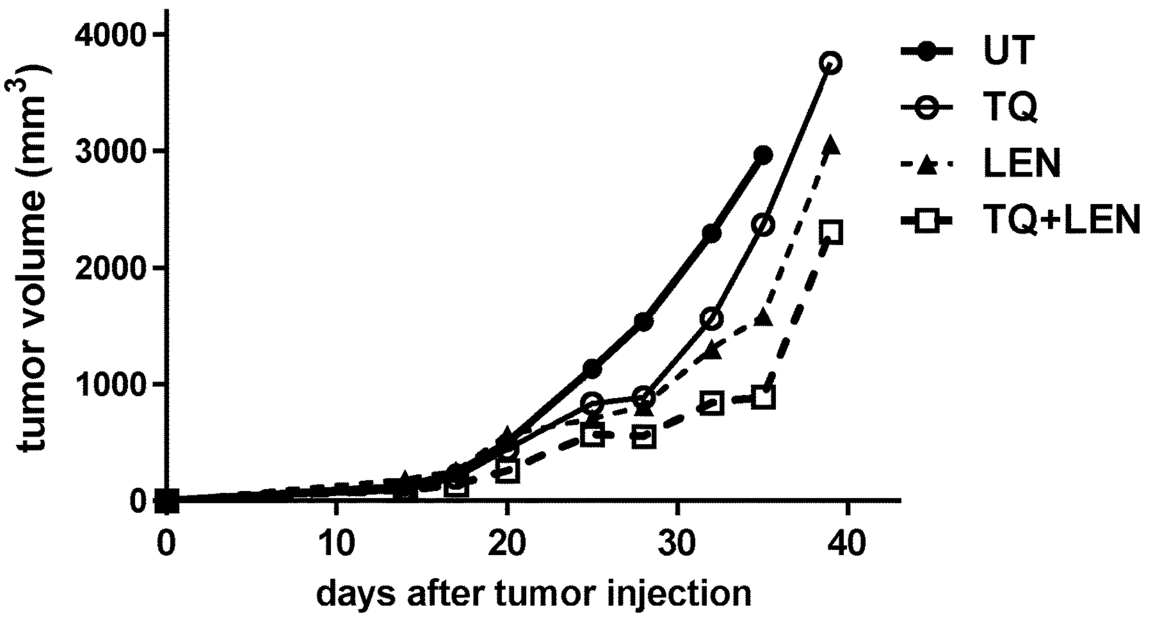
FIG. 2 is a graph showing the tumour volume in mice in the human MM1.S human xenograft model as a function of days of treatment with a combination of tasquinimod and lenalidomide (TQ+LEN) and, for comparison, in mice receiving no treatment (UT), or treatment with tasquinimod only (TQ), or treatment with lenalidomide only (LEN).

Both tasquinimod and lenalidomide reduced the multiple myeloma growth as compared to control mice when given as monotherapies in the MM1.S tumor model (FIG. 2). When combining tasquinimod with lenalidomid, an improvement of the effect was recorded.

Example 3

Use of Tasquinimod in Combination with Lenalidomide

Figure 3:
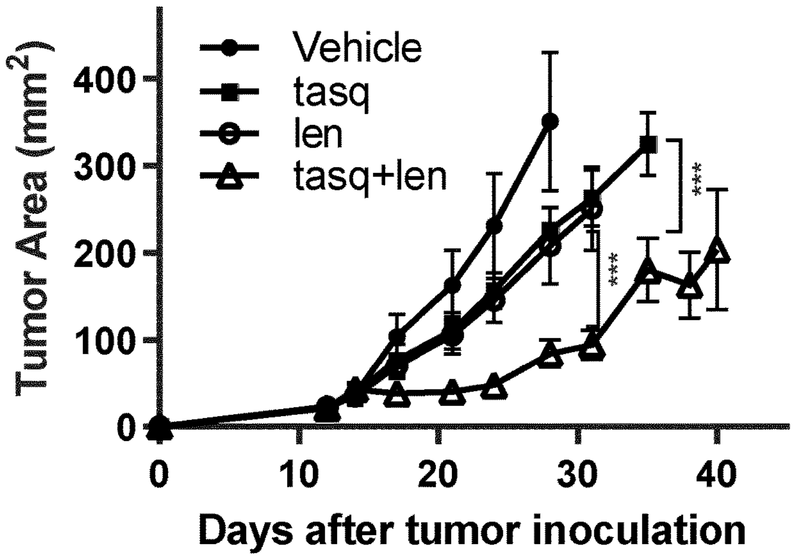
FIG. 3 is a graph showing the tumour area in mice in the human H929 xenograft model as a function of days of treatment with a combination of tasquinimod and lenalidomide (tasq+len) and, for comparison, in mice receiving only vehicle (Vehicle), or treatment with tasquinimod only (tasq), or treatment with lenalidomide only (len).

Human NCI-H929 myeloma cells ($5\times10^6$) were injected s.c. into NSG mice. On day 11 after tumor cell injection mice were split into 4 groups and treated with vehicle (VC); tasquinimod (TQ), 30 mg/kg ad lib in drinking water; lenalidomide (LEN), 20 mg/kg, oral gavage, 5 days on, 2 days off; or the combination of tasquinimod and lenalidomide (TQ+LEN), (TQ, 30 mg/kg ad lib in drinking water; LEN, 20 mg/kg, oral gavage, 5 days on, 2 days off). Tumor growth was evaluated. FIG. 3 shows the results, in terms of tumor growth presented as mean±SEM for each group (n=5 mice per group).

Statistics: two-way ANOVA. VC vs TQ p=0.0516; VC vs LEN p=0.0345; VC vs TQ+LEN p<0.0001; LEN vs LEN+TQ p<0.0001; TQ vs TQ+LEN p<0.0001.

Example 4

Use of Tasquinimod in Combination with Daratumumab

Figure 4:
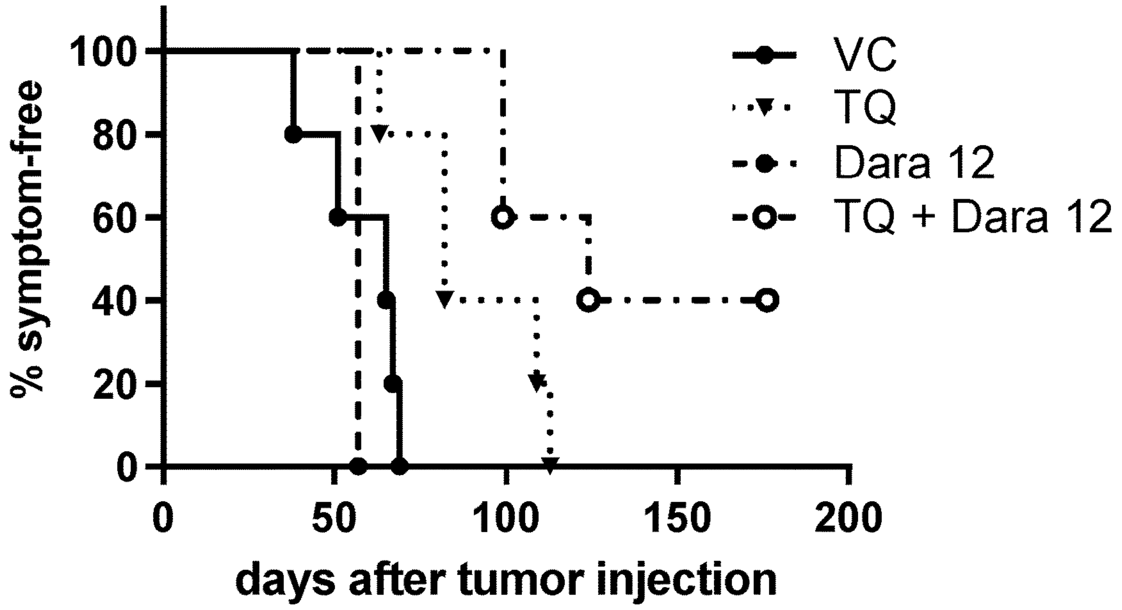
FIG. 4 is a graph showing the % of symptom-free in a group of mice, in a xenograft i.v. RPMI-8226 mouse model of multiple myeloma, as a function of days after tumor inoculation, in mice treated with vehicle (VC), with tasquinimod only (TQ), with daratumumab only (Dara 12), or with a combination of tasquinimod and daratumumab (TQ+Dara 12).
Figure 5:
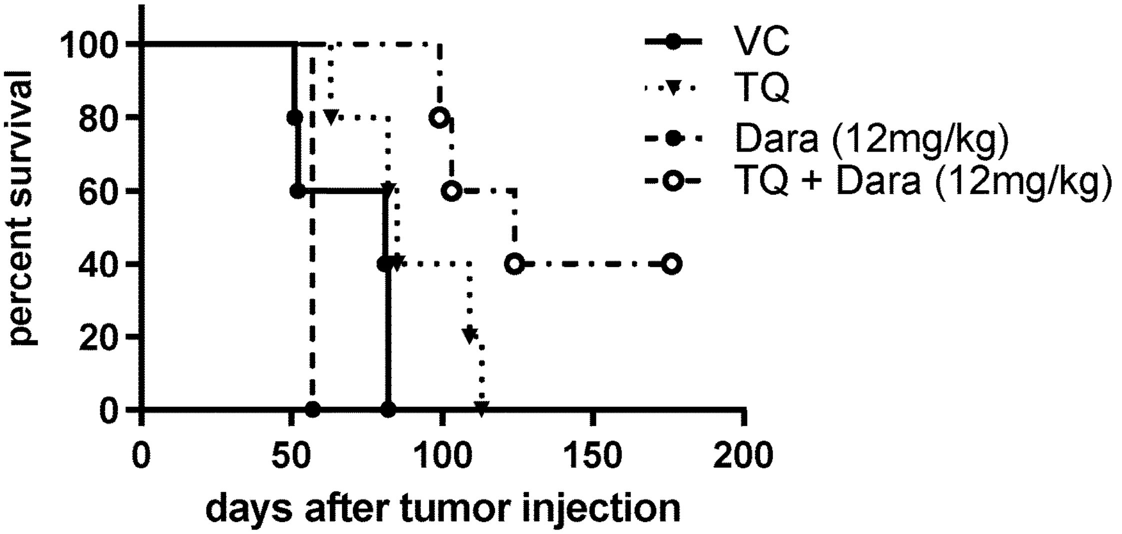
FIG. 5 is a graph showing the percent survival in a group of mice, in a xenograft i.v. RPMI-8226 model of multiple myeloma as a function of days after tumor inoculation, in mice treated with vehicle (VC), with tasquinimod only (TQ), with daratumumab only (Dara 12), or with a combination of tasquinimod and daratumumab (TQ+Dara 12).

RPMI-8226 myeloma cells ($5\times10^6$) were injected i.v in the tail vein of NSG mice. Treatment with tasquinimod (TQ), 30 mg/kg ad lib in drinking water, with daratumumab (Dara) (12 mg/kg, i.p., twice a week), with vehicle only, or with tasquinimod in combination with daratumumab (TQ+Dara) (TQ, 30 mg/kg ad lib in drinking water; Dara, 12 mg/kg, i.p., twice a week), was started on day 7 after tumor injection (n=5 per each group). Development of symptoms and mice survival were evaluated. The results, in terms of % symptom-free mice and in terms of percent surviving mice, are illustrated in FIGS. 4 and 5, respectively. Log-rank test was used for the statistical analysis.

Statistics: Symptoms: VC vs TQ p=0.0197; Dara vs Dara+TQ p=0.0027; TQ vs TQ+Dara p=0.0472; VC vs TQ+Dara p=0.0018. Survival: VC vs TQ p=0.0549; Dara vs Dara+TQ p=0.0027; TQ vs TQ+Dara p=0.0554; VC vs TQ+Dara p=0.0027.

Example 5

Use of Tasquinimod in Combination with Ixazomib

Figure 6:
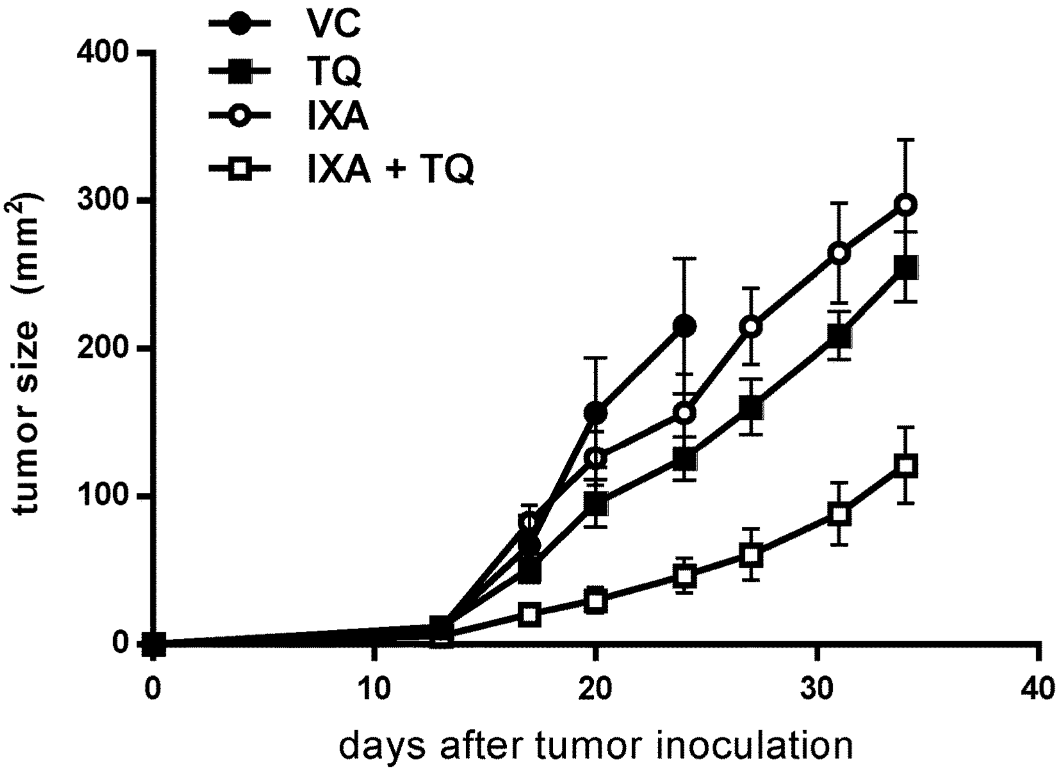
FIG. 6 is a graph showing the tumour size in mice, in the human NCI-H929 xenograft mouse model of multiple myeloma, as a function of days after tumor inoculation, in mice treated with vehicle (VC), with tasquinimod only (TQ), with ixazomib only (IXA), or with a combination of tasquinimod and ixazomib (IXA+TQ).

Human NCI-H929 myeloma cells ($4\times10^6$) were injected s.c. into NSG mice. Mice were assigned to one of 4 groups and treated with vehicle (VC); tasquinimod (TQ), 30 mg/kg ad lib in drinking water; ixazomib (IXA), 5 mg/kg, oral gavage, twice a week; or the combination TQ+IXA (TQ, 30 mg/kg ad lib in drinking water; IXA, 5 mg/kg, oral gavage, twice a week). Treatment with tasquinimod started 8 h after tumor cell injection; treatment with ixazomib started on day 13 after tumor cell injection. Tumor growth was evaluated. The tumor growth presented as mean±SEM for each group (n=10 mice per group) is illustrated in FIG. 6.

Statistics: two-way ANOVA. VC vs TQ p=0.0178; VC vs IXA p=0.2383; VC vs TQ+IXA p<0.0001; IXA vs IXA+TQ p<0.0001; TQ vs IXA+TQ p<0.0001.

Example 6

Use of Tasquinimod in Combination with Lenalidomide

Figure 7:
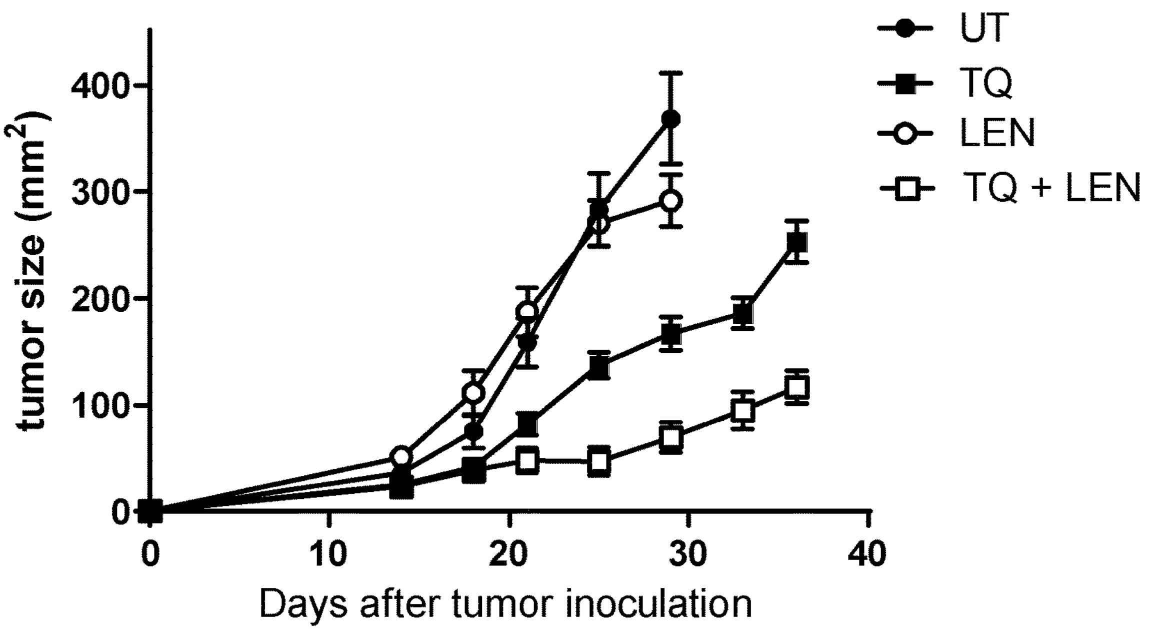
FIG. 7 is a graph showing the tumour size in mice, in the human NCI-H929 xenograft mouse model of multiple myeloma, as a function of days after tumor inoculation, in mice treated with vehicle, i.e. "untreated" (UT), with tasquinimod only (TQ), with lenalidomide only (LEN), or with a combination of tasquinimod and lenalidomide (TQ+LEN).

Human NCI-H929 myeloma cells ($3.5\times10^6$) were injected s.c. into NSG mice. Mice were assigned to one of 4 groups and treated with vehicle, (UT), tasquinimod (TQ), 30 mg/kg ad lib in drinking water, lenalidomide (LEN), 20 mg/kg, oral gavage, 5 days/week, 5 days with and 2 days without lenalidomide treatment, or the combination LEN+TQ. Treatment with TQ started 8 h after tumor cell injection; treatment with lenalidomide started on day 14 after tumor cell injection. Tumor growth was evaluated. The tumor growth presented as mean±SEM for each group (n=10 mice per group, except for the lenalinomide group, where n=6) is illustrated in FIG. 7.

Statistics: two-way ANOVA. UT vs TQ $p<0.0001$; UT vs LEN $p=0.0481$; TQ vs TQ+LEN $p<0.0001$; LEN vs TQ+LEN $p<0.0001$; UT vs TQ+LEN $p<0.0001$.

The invention claimed is:

1. A method of treatment of multiple myeloma in a subject, the method comprising administering to the subject tasquinimod, or a pharmaceutically acceptable salt thereof, in combination with at least one further compound selected from (i) a proteasome inhibitor, (ii) an immunomodulatory imide, and (iii) an antibody, wherein the proteasome inhibitor is selected from bortezomib and ixazomib;

the immunomodulatory imide is lenalidomide; and the antibody is daratumumab.

2. The method according to claim 1, wherein tasquinimod, or the pharmaceutically acceptable salt thereof, and the at least one further compound are administered separately, sequentially or simultaneously.

3. The method according to claim 1, wherein tasquinimod, or the pharmaceutically acceptable salt thereof, is administered in combination with (i) the proteasome inhibitor bortezomib or ixazomib, and optionally a further compound selected from (ii) an immunomodulatory imide, and (iii) an antibody.

4. The method according to claim 3, wherein the proteasome inhibitor is bortezomib.

5. The method according to claim 3, wherein the proteasome inhibitor is ixazomib.

6. The method according to claim 1, wherein tasquinimod, or the pharmaceutically acceptable salt thereof, is administered in combination with (i) the immunomodulatory imide lenalidomide, and optionally a further compound selected from (ii) a proteasome inhibitor, and (iii) an antibody.

7. The method according to claim 1, wherein tasquinimod, or the pharmaceutically acceptable salt thereof, is administered in combination with (i) the proteasome inhibitor bortezomib or ixazomib, and (ii) the immunomodulatory imide lenalidomide, and optionally (iii) an antibody.

8. The method according to claim 7, wherein (i) the proteasome inhibitor is bortezomib.

9. The method according to claim 7, wherein (i) the proteasome inhibitor is ixazomib.

10. The method according to claim 1, additionally comprising administering a corticosteroid.

11. The method according to claim 10, wherein the corticosteroid is selected from dexamethasone and prednisone.

12. The method according to claim 1, wherein the proteasome inhibitor is bortezomib.

13. The method according to claim 1, wherein the proteasome inhibitor is ixazomib.

* * * * *